United States Patent
Foret et al.

(10) Patent No.: US 6,929,731 B2
(45) Date of Patent: Aug. 16, 2005

(54) PARALLEL ARRAY OF INDEPENDENT THERMOSTATS FOR COLUMN SEPARATIONS

(75) Inventors: Frantisek Foret, Malden, MA (US); Barry L. Karger, Newton, MA (US)

(73) Assignee: Northeastern University, Boston, MA (US)

(*) Notice: Subject to any disclaimer, the term of this patent is extended or adjusted under 35 U.S.C. 154(b) by 645 days.

(21) Appl. No.: 09/979,622

(22) PCT Filed: Mar. 7, 2001

(86) PCT No.: PCT/US01/07329
§ 371 (c)(1),
(2), (4) Date: Nov. 6, 2001

(87) PCT Pub. No.: WO01/67080
PCT Pub. Date: Sep. 13, 2001

(65) Prior Publication Data
US 2002/0157951 A1 Oct. 31, 2002

Related U.S. Application Data
(60) Provisional application No. 60/187,517, filed on Mar. 7, 2000.

(51) Int. Cl.[7] ............................................. C02F 11/18
(52) U.S. Cl. ....................... 204/602; 204/621; 204/601
(58) Field of Search .............................. 204/602, 621, 204/601

(56) References Cited

U.S. PATENT DOCUMENTS

| | | | |
|---|---|---|---|
| 5,085,757 A | * | 2/1992 | Karger et al. ............... 204/603 |
| 5,413,686 A | | 5/1995 | Klein et al. ............. 204/299 R |
| 5,641,400 A | * | 6/1997 | Kaltenbach et al. ...... 210/198.2 |
| 5,716,842 A | | 2/1998 | Baier et al. ............... 435/283.1 |
| 5,885,430 A | | 3/1999 | Kernan et al. ............... 204/453 |
| 5,965,410 A | | 10/1999 | Chow et al. ................ 435/91.2 |
| 6,120,667 A | | 9/2000 | Hayashizaki et al. ........ 204/603 |
| 6,225,061 B1 | | 5/2001 | Becker et al. .................. 435/6 |

FOREIGN PATENT DOCUMENTS

| | | | |
|---|---|---|---|
| EP | 1 228 804 A2 | 8/2002 | .............. B01L/7/00 |
| WO | WO 99/41015 | 8/1999 | .............. B01L/7/00 |

* cited by examiner

Primary Examiner—Ling-Sui Choi
(74) Attorney, Agent, or Firm—Weingarten, Schurgin, Gagnebin & Lebovici LLP

(57) ABSTRACT

A thermostat array including an array of two or more capillary columns (10) or two or more channels in a microfabricated device is disclosed. A heat conductive material (12) surrounded each individual column or channel in array, each individual column or channel being thermally insulated from every other individual column or channel. One or more independently controlled heating or cooling elements (14) is positioned adjacent to individual columns or channels within the heat conductive material, each heating or cooling element being connected to a source of heating or cooling, and one or more independently controlled temperature sensing elements (16) is positioned adjacent to the individual columns or channels within the heat conductive material. Each temperature sensing element is connected to a temperature controller.

11 Claims, 4 Drawing Sheets

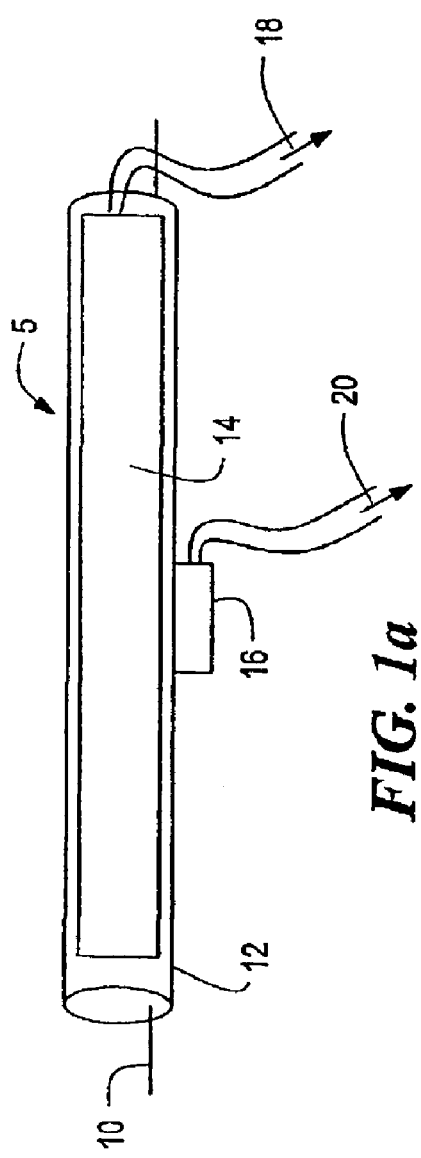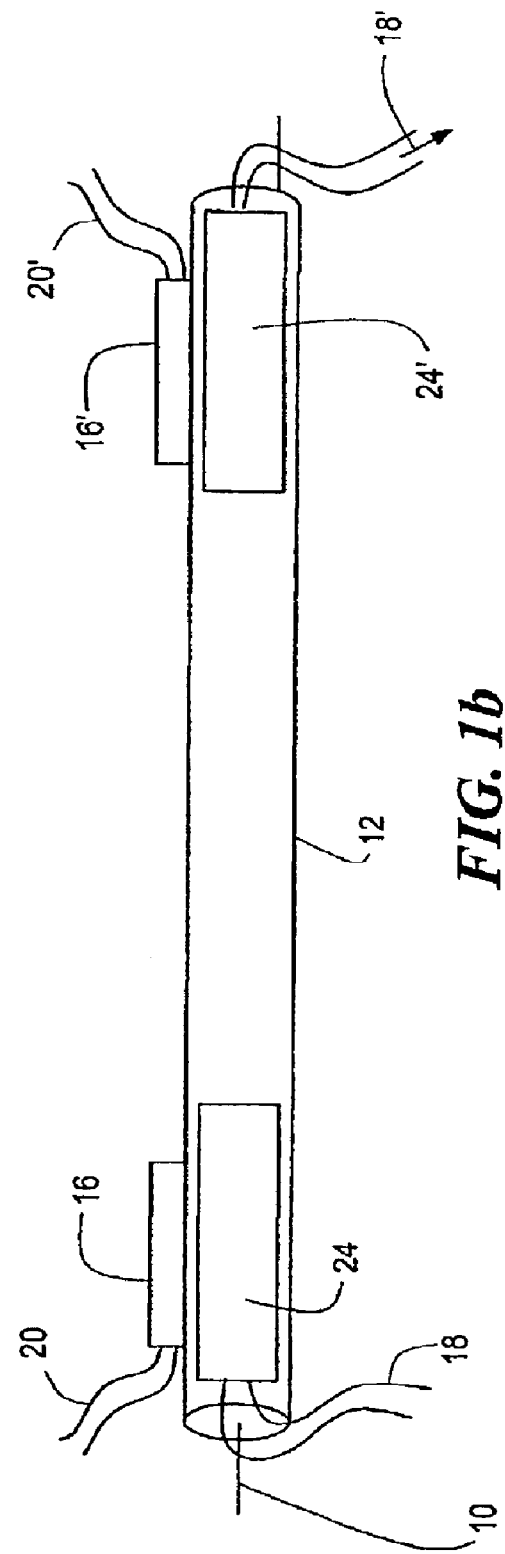

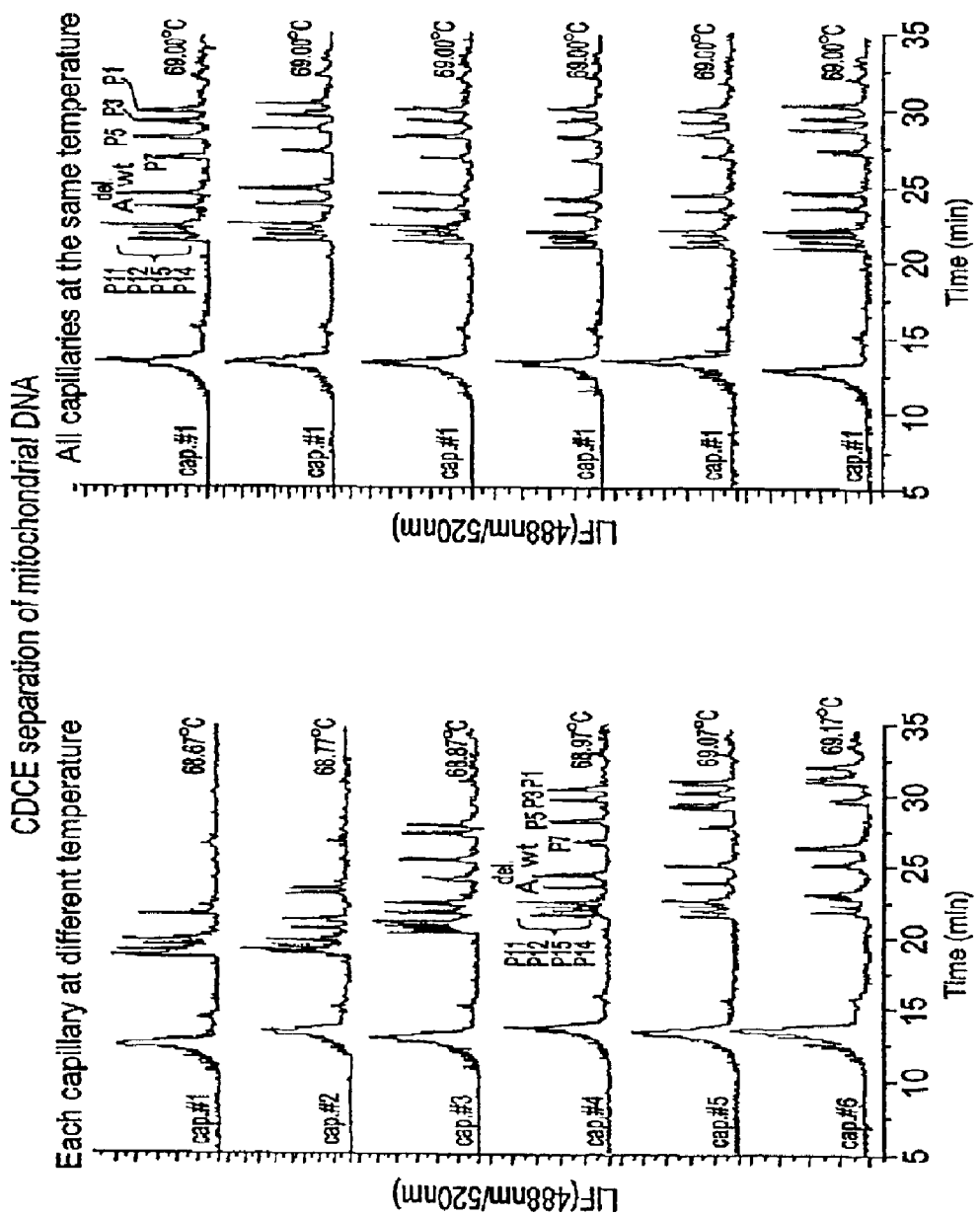

US 6,929,731 B2

PARALLEL ARRAY OF INDEPENDENT THERMOSTATS FOR COLUMN SEPARATIONS

CROSS REFERENCE TO RELATED APPLICATIONS

This application claims the priority of U.S. Provisional Application No. 60/187,517 filed Mar. 7, 2000 entitled, PARALLEL ARRAY OF INDEPENDENT THERMOSTATS FOR COLUMN SEPARATIONS, the whole of which is hereby incorporated by reference herein.

STATEMENT REGARDING FEDERALLY SPONSORED RESEARCH OR DEVELOPMENT

Part of the work leading to this invention was carried out with United States Government support provided under a grant from the Department of Energy, Grant No. DE-FG02-90ER60985. Therefore, the U.S. Government has certain rights in this invention.

BACKGROUND OF THE INVENTION

Recent advances in the biological sciences require new approaches for high throughput analytical systems. One way to achieve high throughput is to use multiple capillary electrophoresis separation columns run in parallel. For example, over one hundred separation columns are currently used in capillary array DNA sequencers. Similar systems may be used for other applications, such as protein and peptide analysis and/or analysis of small molecules. Many other separation principles besides capillary electrophoresis, such as liquid chromatography, electrochromatography, extraction, etc., are also useful for analysis of molecular components of biological systems and are amenable to multiplexing in some form of an array. Such arrays may be composed, e.g., of individual columns (or groups of individual columns) or may be completely integrated, for example on a microfabricated device. To ensure stable physico-chemical conditions during a separation procedure, the array must be operated under a defined constant or programmed temperature or temperature gradient. In existing DNA sequencers or analyzers, for example, all of the separation columns are held at the same temperature.

BRIEF SUMMARY OF THE INVENTION

In the analysis of samples requiring identical (or similar) separation conditions, it may be useful to have all of the components of an array, e.g., all of the separation columns of a DNA sequencer or analyzer as discussed above, held at the same temperature. On the other hand, there are many cases where the possibility of adjusting the run temperature individually for each separation element of an array would be of great practical importance. For example, an array of ten capillary columns, operating at ten different temperatures, could be used to find an optimum separation temperature for a given sample, resulting in a ten fold increase in productivity for finding that optimum temperature. In addition, ten different samples each requiring a different temperature for optimum analysis could be run in parallel with a similar increase in productivity beyond what individual sample runs carried out consecutively would achieve. The system of the invention provides an efficient way of achieving such productivity increases.

Thus, in one aspect the invention is directed to a thermostat array that includes two or more capillary columns or two or more channels in a microfabricated device, wherein the two or more columns or the two or more channels are associated in an array; a heat conductive material surrounding each individual column or channel, each individual column or channel being thermally insulated from every other individual column or channel; one or more independently controlled heating or cooling elements positioned adjacent to individual columns or channels within the heat conductive material, each heating or cooling element being connected to a source of heating or cooling; and one or more independently controlled temperature sensing elements positioned adjacent to individual columns or channels within the heat conductive material, each temperature sensing element being connected to a temperature controller.

In another embodiment, multiple columns (or channels) are heated or cooled by a single heating or cooling element and clusters of such columns or channels are associated in a thermostat array of the invention wherein different clusters within the array are independently controlled.

Preferably, the capillary columns or channels in a microfabricated device are intended for use in a separation method calling for an electric field and the columns or channels are electrically isolated from the heating/cooling elements, the heating/cooling elements surround the capillary columns or channels, and the electronic elements of the thermostat array are solid state. The heating or cooling elements may be positioned so as to induce a thermal gradient along the length of the column or channel.

The thermostat array of the invention provides a highly efficient way to enhance productivity in processing multiple, different samples that require different temperatures for the required analyses. The array set-up described can be implemented in both multiple capillary column and microchip format. Using the system of the invention, a run temperature can remain stable to within 0.01–0.02° C.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 1a shows one embodiment of an individual capillary column with an associated individually controlled solid-state thermostat suitable for use in the thermostat array according to the invention;

FIG. 1b shows another embodiment of an individual capillary column with an associated individually controlled solid-state thermostat suitable for use in the thermostat array according to the invention;

FIGS. 5a and 5b are graphs showing the results from the use of the thermostat array according to the invention for optimization of CDCE separation of mitochondrial DNA.

DETAILED DESCRIPTION OF THE INVENTION

Figure 2:
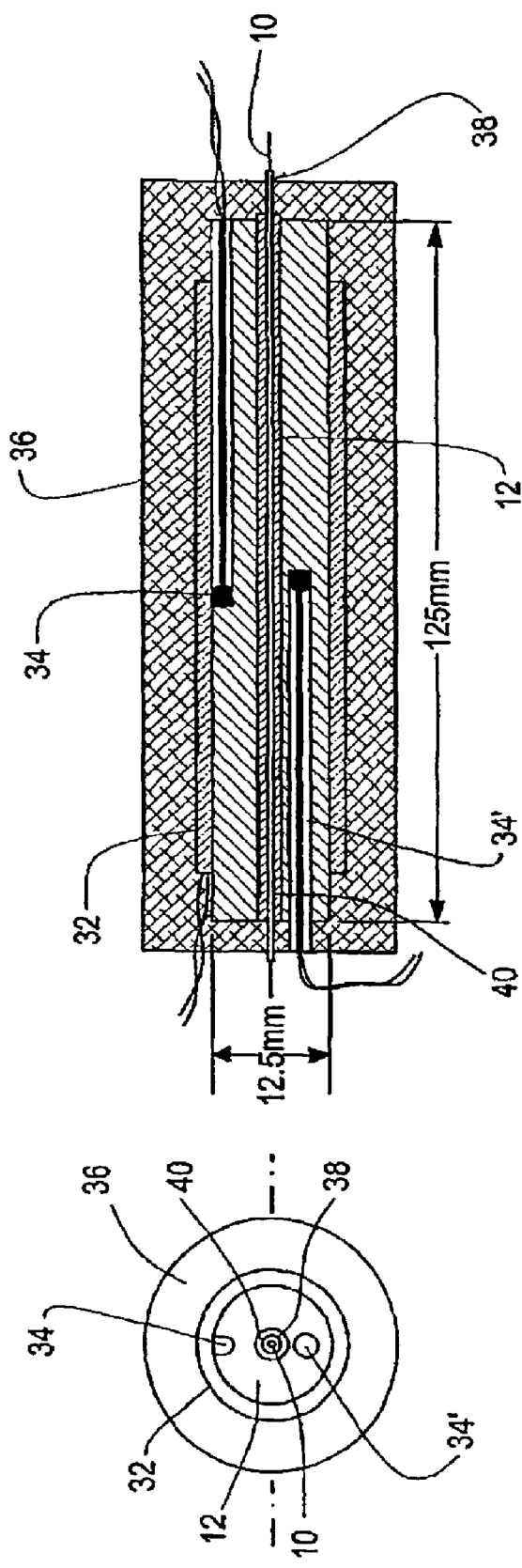
FIG. 2 shows in more detail another embodiment of an individual capillary column with an associated individually controlled solid-state thermostat suitable for use in the thermostat array according to the invention.

Presented here is an array of independently controlled thermostats for column separations. Individual thermostats in the array are associated with individual capillary columns (or channels in a microfabricated device) or with groups (clusters) of such columns or channels. An array of independently controlled thermostats according to the invention is useful, e.g., in constant denaturant capillary electrophoresis as described in K. Khrapko et al., *Constant Denaturant Capillary Electrophoresis (CDCE): A High Resolution Approach to Mutational Analysis.* Nucl. Acid. Res., 22, 1994, 364–269. In CDCE, DNA fragments are analyzed based on differences in melting temperature. Specific embodiments of individual capillary columns with associated individually controlled solid-state thermostats suitable for use in the thermostat array of the invention are shown in FIGS. 1a and 1b.

Referring to FIG. 1a, a separation column 10 is enclosed in a thermostat or heater body 12 made of a good thermal conductor (e.g., copper, heat conducting plastic, conducting ceramic or glass), which includes a flexible heating element 14. The temperature generated in the thermostat body is sensed by a temperature sensor 16 (e.g., RTD sensor, thermocouple, thermistor or optical temperature sensor). Wires 18 connect heating element 14 to a source of heating current (not shown), and wires 20 connect temperature sensor 16 to a temperature controller (not shown), which has feedback connection to the current source. This solid-state thermostat can be used either for maintaining a stable column temperature or for temperature programming when timed temperature changes are required in a particular analysis.

As depicted in FIG. 1a, heating element 14 surrounds column 10. In alternative designs, multiple, discrete heating elements can be used to transfer heat uniformly to all portions of the column, along its length. Similarly, multiple temperature sensor elements, analogous to element 16, can be utilized. The heating elements and temperature sensors can be placed on the surface of the thermostat body or can be embedded inside of it. In either case, good thermal contact should be maintained with the column during the operation. In some cases, the whole thermostat body can be made of electrically conductive material (e.g., conductive plastic, ceramic or semiconductor) and serve as the heating element when conducting electric current. To prevent the need for extremely high electric currents, the thermostat body in this case should have an end to end resistance larger than ~0.1 Ohm. Other designs for individually controlled thermostat bodies for the thermostat array of the invention, such as designs using circulating fluid for temperature control, e.g., a liquid such as would be provided by a miniaturized water bath or a gas such as a warm air stream, are also appropriate. In general, any thermostat body design that has a heating (or cooling) element in thermal contact with the capillary column (or channel) is suitable for use in the thermostat of the invention. When separation is to be carried out in an electric field, the thermostat body must be electrically isolated from the capillary column or the source of heating or cooling must be such as not to generate an electric field.

Another alternative design for an individual solid-state thermostat/associated column combination for use in the thermostat array of the invention is shown in FIG. 1b. This design is suitable for creating a temperature gradient between two different temperatures along the separation column. Referring to FIG. 1b, a separation column 10, similar to that depicted in FIG. 1a, is enclosed in a thermostat or heater body 12. Two individual flexible heating or cooling elements 24,24' (e.g., resistive heaters or Peltiere elements) are positioned near either end of thermostat body 12 and are individually connected to a source of heating current (not shown) by wires 18,18'. (A greater number of heating/cooling elements could also be used.) The temperature generated at either end of the thermostat body is sensed by temperature sensors 16,16', which are positioned on the body near heating elements 24,24', respectively. Wires 20,20' connect temperature sensors 16,16', respectively, to a temperature controller (not shown), which has feedback connection to the current source. By means of this heating element-temperature sensor-current supply loop, heating/cooling elements 24,24' keep the temperature in the thermostat body in the regions of their attachment constant and different. Due to thermal conduction, a temperature gradient develops along the thermostat body between the positions of heating/cooling elements 24,24'.

An individual capillary column with associated solid-state thermostats suitable for use in the thermostat array of the invention is shown in more detail in FIG. 2. Referring to FIG. 2, an individual solid state thermostat 30 for a capillary column for use in a thermostat array of the invention includes a copper rod heater body 12 surrounded by flexible heater 32, which ih turn is surrounded by thermal insulation jacket 36, made from polyurethane foam. Two thermistors 34,34' for independent temperature control and monitoring, are positioned in a groove or a hole on the outer edges of heater body 12. A stainless steel capillary 38, with an internal diameter (e.g., 400 μm) just slightly larger than the outer diameter of separation capillary 10 (e.g., 375 μm) and containing separation capillary 10, is glued in the center of heater body 12, in hole 40 (e.g., 2.8 mm in diameter), using a heat conductive, electrically non-conductive epoxy. The two thermistors 34,34' can be used for precise temperature adjustment and monitoring. In this example, one thermistor, e.g., 34, is used to sense the temperature in the heater body and to provide a feedback signal to the heater control unit while the second thermistor, e.g., 34', is used for periodic monitoring of the temperature with a calibrated electronic thermometer. The second thermistor is used from time to time to calibrate the electronic 5 thermometer as, as a practical matter, temperature drift can occur after numerous runs using a specific system have been carried out. This thermistor can be made to be removable (movable between several heaters) so that the same thermistor can be used with the calibrated electronic thermometer to monitor the temperature in several heaters.

The example described above shows a heater suitable for an array of discrete capillaries. Independent control of temperature is also important in microfabricated devices. The entire thermostat/capillary column array described here, including heaters and sensors (thermistors, RTDs, etc.) and, if needed, also the controllers, can be integrated on a microfabricated device, e.g., a microchip. Due to the small size of microchips and the good thermal conductivity of most substrate materials used for fabrication, e.g., fused silica, the closely neighboring heated/cooled areas of the thermostat array could strongly influence each other. To prevent this type of thermal communication, microdevices implemented with the thermostat array of the invention need to be equipped with heat insulating regions between individual temperature controlled channels. An example of such a microdevice is depicted in FIG. 3.

Figure 3:
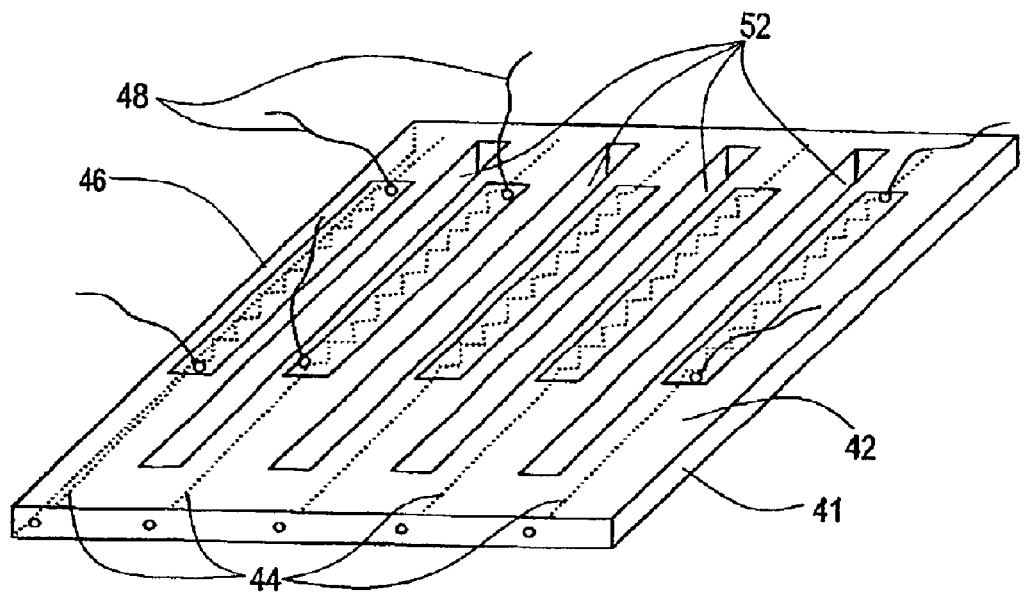
FIG. 3 shows an embodiment of the thermostat array according to the invention integrated on a microfabricated device.

Referring to FIG. 3, planar microchip 41, having a fused silica chip body 42, contains multiple channels 44, each associated with a heating/cooling element 46. Wires 48 connect heating/cooling elements to a source of current. To eliminate heat transfer between individual channel/heating element combinations, through cuts 52 are made between the channels. The cuts can be further filled with an insulating material such as polyurethane or polystyrene foam. Heating elements 46 can be attached from the top and/or the bottom of the microchip. In addition, the vertical walls of cuts 52 could be coated with a conductive material and connected to the current source so as to provide a source of heating/cooling surrounding a desired channel.

The temperature sensors (Pt, thermistors), not shown, can be attached from either side of a channel 44. Alternatively, the heating element itself can serve as the temperature sensing element if it is made from a material that changes resistance over time. For example, a conductive (Pt, Cr, Au, conductive plastic) layer can be deposited directly on the surface of the microdevice (or inside before the layers of the device are bonded) by using sputtering or chemical vapor deposition techniques. Similarly to the earlier described configuration for capillary column thermostat arrays, multiple channels could also be heated (cooled) by a single heating/cooling element, and clusters of such channels could be associated in a thermostat array of the invention wherein different clusters within the array are independently controlled.

Figure 4:
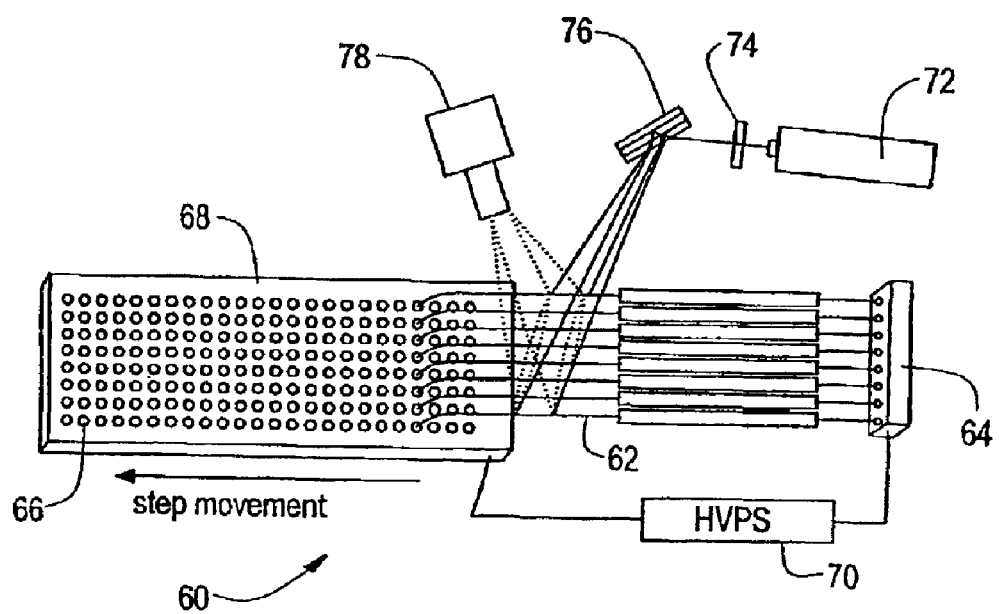
FIG. 4 shows an example of the use of the thermostat array according to the invention for CDCE analysis.

An example of the use of the thermostat array of the invention in a system for CDCE analysis is shown in FIG. 4. Referring to FIG. 4, solid state thermostat array 60 includes separation capillaries 62 for CDCE analysis, e.g., of separate mitochondrial DNA samples. The samples are injected into individual capillaries 62, which are then connected to buffer reservoir 64. The capillaries are also positioned for comprehensive collection of zones exiting the capillaries into microwells 66 on gel plate 68, which is movable on a moterized stage relative to the exit end of the capillaries. Other features of the system of FIG. 4 include a high voltage power supply 70, a laser illumination system 72, with associated line generator 74 and beam splitter 76. The laser system produces two point illumination for, e.g., laser induced fluorescence (LIF) detection using a spectrograph/CCD detector 78. In this particular design, the thermostats are used to maintain a constant temperature in each separation capillary (a different temperature in each column) to achieve the desired resolution of the DNA fragments, which are consecutively subjected to LIF velocity measurement and fraction collection.

Results from the use of the thermostat array of the invention with included capillary columns for optimization of CDCE separation of mitochondrial DNA are given in FIGS. 5a and 5b. The separation can be optimized by operating individual capillaries at different temperatures (note that a very small temperature change causes a large change in separation) as shown in FIG. 5a. Since the same sample can be analyzed simultaneously at multiple different temperatures (six in the example shown here), a significant increase in the information throughput about the sample properties is achieved (here, information as to the optimum temperature for separation). If all thermostats are set to the same temperature (as is common in current capillary array instrumentation), a reproducible analysis can be obtained in all the capillaries (as is shown in FIG. 5b); however, only one type of information is obtained, i.e., the sample properties at only one temperature, and more time is required to obtain information for run temperature optimization.

The example shown here applies to CDCE. However, many other separation techniques employing more than one separation column, such as in DNA sequencing, liquid chromatography, enzyme reaction columns or extraction columns would also benefit from use of the thermostat array of the invention. Other systems amenable for study using the thermostat array of the invention include single stranded conformational polymorphisms (SSCP) and non-covalent complexes, which are temperature sensitive.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A thermostat array comprising:

two or more capillary columns or two or more channels in a microfabricated device, wherein said two or more columns or said two or more channels are associated in an array;

a heat conductive material surrounding each individual said column or channel, wherein each individual said column or channel is thermally insulated from every other individual said column or channel;

one or more independently controlled heating or cooling elements positioned adjacent to individual said columns or channels, within said heat conductive material, wherein each heating or cooling element is connected to a source of heating or cooling; and one or more independently controlled temperature sensing elements positioned adjacent to individual said columns or channels, within said heat conductive material, wherein each temperature sensing element is connected to a temperature controller.

2. The array of claim 1, wherein said one or more heating or cooling elements are also used as said temperature sensing elements.

3. The array of claim 1, wherein said capillary columns or channels in a microfabricated device are suitable for use in a separation method calling for an electric field and said columns or channels are electrically isolated from said heating or cooling elements.

4. The array of claim 1, wherein said heating or cooling elements surround said capillary columns or channels.

5. The array of claim 1, comprising two or more independently controlled heating or cooling elements associated with an individual said column or channel, wherein said two or more heating or cooling elements are positioned along said associated column or channel so as to be capable of inducing a thermal gradient along the length of said column or channel.

6. The array of claim 1, wherein said independently controlled heating or cooling elements associated with an individual said column or channel are configured for temperature programming.

7. The array of claim 1, wherein said heating or cooling elements are solid-state.

8. The array of claim 1, wherein said heating or cooling elements are a fluid.

9. The array of claim 8, wherein said fluid heating or cooling element is a liquid.

10. The array of claim 8, wherein said fluid heating or cooling element is a gas.

11. A thermostat array comprising:

multiple capillary columns or multiple channels in a microfabricated device, wherein said multiple columns or said multiple channels are associated in an array;

a heat conductive material surrounding each individual said column or channel, wherein each individual said column or channel is thermally insulated from every other individual said column or channel;

one or more independently controlled heating or cooling elements positioned adjacent to individual said columns or channels, within said heat conductive material, wherein each heating or cooling element is connected to a source of heating or cooling; and one or more independently controlled temperature sensing elements positioned adjacent to individual said columns or channels, within said heat conductive material, wherein each temperature sensing element is connected to a temperature controller and wherein two or more of said multiple columns or channels are heated or cooled by a single heating or cooling element and multiple clusters of such columns or channels heated or cooled by a single heating or cooling element are associated in said thermostat array and wherein said columns or channels heated or cooled by a single heating or cooling element within a cluster of said columns or channels can be maintained at the same temperature and different clusters within said array are independently controllable.

* * * * *

UNITED STATES PATENT AND TRADEMARK OFFICE
CERTIFICATE OF CORRECTION

PATENT NO.      : 6,929,731 B2  
APPLICATION NO. : 09/979622  
DATED           : August 16, 2005  
INVENTOR(S)     : Frantisek Foret et al.

It is certified that error appears in the above-identified patent and that said Letters Patent is hereby corrected as shown below:

On Title Page Item (57) col. 1, Abstract (57), line 4, "surrounded" should read --surrounds--; and Column 4, line 39, delete "5".

Signed and Sealed this

Fifteenth Day of August, 2006

JON W. DUDAS  
*Director of the United States Patent and Trademark Office*